United States Patent [19]

Keiner

[11] Patent Number: 5,238,829
[45] Date of Patent: Aug. 24, 1993

[54] MICROBIOLOGICAL PROCESS FOR THE PRODUCTION OF 6-HYDROXYPYRAZINECARBOXYLIC ACID

[75] Inventor: Andreas Keiner, Visp, Switzerland

[73] Assignee: Lonza Ltd., Gampel/Valais, Switzerland

[21] Appl. No.: 936,201

[22] Filed: Aug. 27, 1992

[30] Foreign Application Priority Data

Aug. 30, 1991 [CH] Switzerland ............... 2556/91

[51] Int. Cl.$^5$ ............... C12P 17/12; C12P 7/42; C12N 1/12
[52] U.S. Cl. ............... 435/122; 435/146; 435/252.1; 435/829
[58] Field of Search ............... 435/122, 829, 252.1, 435/146, 253.3

[56] References Cited

PUBLICATIONS

O. Shukla and S. M. Kaul, Indian J. of Biochemistry and Biophysics, (1973), vol. 10, pp. 1 to 76.
O. Shukla et al., Indian J. of Biochemistry and Biophysics, vol. 14, (19877), pp. 292 to 295.
R. L. Tate and J. C. Ensign, Can. Jan. Microbiol., vol. 20., (1974), pp. 695 to 702.
Rompps-Chemie-Lexikon, vol. 5, (1987), p. 3411.
Experimental Parasitology, 57, (1984), pp. 55 to 61.
Chemical Abstracts, vol. 66, No. 094996.
Ohsugi et al. Agric. Biol. Chem (1981), 45, pp. 1879-1880.

Primary Examiner—Douglas W. Robinson
Assistant Examiner—J. Sevigny
Attorney, Agent, or Firm—Fisher, Christen & Sabol

[57] ABSTRACT

A microbiological process for the production of 6-hydroxypyrazinecarboxylic acid and/or its salts with microorganisms using picolinic acid and/or its salts. The microorganisms grow with picolinic acid and/or its salts as the sole carbon, nitrogen and energy source. In this way the formed 6-hydroxypyrazinecarboxylic acid is accumulated in the medium and then isolated.

7 Claims, No Drawings

MICROBIOLOGICAL PROCESS FOR THE PRODUCTION OF 6-HYDROXYPYRAZINECARBOXYLIC ACID

BACKGROUND OF THE INVENTION

1. Field Of The Invention

The invention relates to a new process for the production of 6-hydroxypyrazinecarboxylic acid and/or its salts with picolinic acid and/or its salts using microorganisms starting from pyrazinecarboxylic acid and/or its salts.

2. Background Art

6-Hydroxypyrazinecarboxylic acid can be used, for example, for the production of structural analogs of the antitubercular agent pyrazinamide (2-pyrazinecarboxylic acid amide), [Rompps-Chemie-Lexikon, volume 5, (1987), page 3411] or for the production of 1,6-dihydro-6-oxo-2-pyrazinecarboxylic acid-4-oxide, which represents an active ingredient for the control of mineral infections [Experimental Parasitology, 57, (1984), pages 55 to 61].

A 3-stage chemical process for the production of 6-hydroxypyrazinecarboxylic acid is described, for example, starting from pyrazinecarboxylic acid methyl ester-4-oxide, in Chemical Abstracts, Vol. 66, No. 094996.

So far no microbiological process for the production of 6-hydroxypyrazinecarboxylic acid is known.

BROAD DESCRIPTION OF THE INVENTION

The object of the invention is to provide a simple economical and ecological process for the production of 6-hydroxypyrazinecarboxylic acid. Other objects and advantages of the process of the invention are set out herein or are obvious herefrom to one skilled in the art.

The objects and advantages of the invention are achieved by the process of the invention.

The invention involves a microbiological process for the production of 6-hydroxypyrazinecarboxylic acid and/or its salts. The pyrazinecarboxylic acid and/or its salts as the substrate with microorganisms, which grow with picolinic acid and/or its salts as the sole carbon, nitrogen and energy source, are converted into 6-hydroxypyrazinecarboxylic acid and/or its salts. The latter is accumulated in the medium.

Preferably the reaction is performed with microorganisms of genera Pseudomonas and/or Arthrobacter and/or Bacillus and/or Alcalioenes and/or Aerococcus and/or Rhodotorula. Preferably the reaction is performed with microorganisms of the species *Alcaligenes faecalis* DSM No. 6269 or their descendants or mutants. Preferably the reaction takes place with a single or continuous substrate addition, so that the substrate concentration does not exceed (i.e., a maximum of) 20 percent by weight. Preferably the reaction is performed under aerobic conditions at a pH of 4 to 10 and at a temperature of 10° to 60° C. Preferably the 6-hydroxypyrazinecarboxylic acid is isolated in the form of slightly soluble salts.

DETAILED DESCRIPTION OF THE INVENTION

Below, by picolinic acid, pyrazinecarboxylic acid and 6-hydroxypyrazinecarboxylic acid is also understood to include their salts such as, their alkali salts or ammonium salts.

According to the invention, pyrazinecarboxylic acid as the substrate is converted with microorganisms, which grow with picolinic acid as the sole carbon, nitrogen and energy source, into 6-hydroxypyrazinecarboxylic acid, and the latter is accumulated in the medium.

In principle all microorganisms which catabolize picolinic acid via 6-hydroxypicolinic acid are suitable for the process. These microorganisms can be isolated with the help of usual microbiological techniques, for example, from sewage sludge with picolinic acid as the growth substrate. Suitably those microorganisms of the genus Pseudomonas. Arthrobacter, Alcalioenes, Aerococcus, Bacillus or Rhodotorula are used, which are already described in the following bibliographic references: O. Shukla and S. M. Kaul, Indian J. of Biochemistry and Biophysics, Vol. 10, pages 176 to 178, O. Shukla et. al., Indian J. of Biochemistry and Biophysics, Vol. 14, (1977), pages 292 to 295, and R. L. Tate and J. C. Ensicn. Can. J. Microbiol., Vol. 20, (1974), pages 695 to 702. The reaction can be performed, sterile or non-sterile, with mixtures as well as with pure isolates of these microorganisms. Also the descendants and mutants of the microorganisms are suitable for the process.

Preferably the process is performed with *Alcaigenes faecalis* DSM No. 6260 as well as the descendants and mutants thereof. The microorganisms of the species *Alcaligenes faecalis* DSM No. 6269 were deposited on Dec. 7, 1990, in the Deutsche Sammlung von Mikroorganismen und Zellkulturen GmbH [German Collection for Microorganisms and Cell Cultures GmbH], Mascheroderweb 1b, D-3300 Brunswick, Germany.

The scientific (taxonomic) description of *Alcaligenes faecalis* DSM 6269 is:

| | |
|---|---|
| cell form | rod |
| width, μm | 0.5 to 0.8 |
| length, μm | 1.0 to 2.0 |
| mobility | + |
| cilicia | peritrichal |
| gram reaction | − |
| lysis by 3% KOH | + |
| aminopeptidas (Cerny) | + |
| spores | − |
| oxidase | + |
| catalase | + |
| growth | |
| anaerobe | − |
| 37°/40° C. | +/− |
| pH 5.6 | + |
| MacConkey Agar | + |
| Pigments | − |
| not diffused | − |
| diffused | − |
| fluorescent | − |
| pyocyanin | − |
| Acid from (OF-Test) | |
| glucose aerobe | − |
| glucose anaerobe | − |
| xylose aerobe | − |
| gas from glucose | − |
| acid from (ASS) | |
| glucose | − |
| fructose | − |
| xylose | − |
| ONPG | − |
| ADH | − |
| LDC | − |
| VP | − |
| indole | − |
| ODC | − |
| $NO_2$ from $NO_3$ | − |

-continued

| | |
|---|---|
| denitrification | − |
| phenylalaninedesaminase | − |
| levan from saccharose | − |
| lecithinase | − |
| urease | − |
| hydrolysis of | |
| starch | − |
| gelatine | − |
| casein | − |
| DNA | − |
| Tween 80 | − |
| aesculin | − |
| tyrosine catabolism | − |
| catabolism | − |
| use of substrates | |
| acetate | + |
| adipate | − |
| caprate | + |
| citrate | + |
| glycolate | + |
| L-lactate | + |
| laevulinate | − |
| malate | + |
| malonate | + |
| phenyl acetate | + |
| propionate | + |
| suberate | − |
| L-arabinose | − |
| fructose | − |
| glucose | − |
| mannose | − |
| maltose | − |
| xylose | − |
| ribose | − |
| mannitol | − |
| gluconate | − |
| 2-ketogluconate | − |
| N-acetylglucosamine | − |
| L-histidine | − |
| L-methionine | + |
| hydroxybutyrate | + |

Usually, before the actual reaction, both the culture (cultivation) and the induction of the microorganisms is performed with picolinic acid. Preferably, the cultivation (culture) and the induction take place with picolinic acid as the sole carbon, nitrogen and energy source.

Before the addition of the substrate (pyrazinecarboxylic acid), the microorganisms then can either be harvested by usual separating processes and resuspended in a fresh medium or the substrate (pyrazinecarboxylic acid) can be added directly to the microorganisms in the original growth medium. For the actual process, then the cell suspension suitably is adjusted to an optical density, at 650 nm, of 1 to 100, preferably 10 to 30.

As the media, those usual among experts can be used both for the cultivation and for the actual reaction. Preferably the medium whose composition is given in Table 1 below is used.

The substrate (pyrazinecarboxylic acid) can be added once or continuously. Suitably, the substrate addition takes place so that the substrate concentration does not exceed 20 percent by weight, preferably 5 percent by weight. Usually the reaction of pyrazinecarboxylic acid and/or its salts to 6-hydroxypyrazinecarboxylic acid and/or its salts takes place with dormant cells. Suitably the reaction is performed under aerobic conditions at a pH of 4 to 10, preferably at a pH of 6 to 8. The temperature suitably is between 10° and 60° C., preferably between 15° and 45° C.

After a usual reaction time of 4 to 100 hours, the product can be obtained by working-up methods usual to one skilled in the art. For example, the product can be isolated in the form of slightly soluble salts. In this case a salt, such as, barium chloride, can be added to formed 6-hydroxypyrazinecarboxylic acid, and then the slightly soluble di-6-hydroxypyrazinecarboxylic acid barium salt is formed and precipitates. In principle, alkaline-earth salts and salts of the copper group, such as, copper and silver, are suitable for the precipitation of slightly soluble salts of 6-hydroxypyrazinecarboxylic acid.

EXAMPLE 1

Cultivation of the biomass

*Alcaligenes faecalis* DSM No. 6269 was cultivated in a mineral salt medium (Table 1) under a continuous addition of sodium picolinate (0.6 g/1/h) in a fermenter at a pH of 7.0 and at a temperature of 30° C. up to an optical density, at 650 nm, of 10.

Biotransformation

Then the cells were centrifuged off and resuspended in 2 liters of a solution containing 0.4 mol (58.87 g) of pyrazinecarboxylic acid sodium salt, pH 7.0. The optical density at 650 nm was then 20. After an incubation time of 16 hours under aerobic conditions at pH 7.0 and a temperature of 30° C., no feedstock was able to be detected anymore by UV-spectroscopy. Then the cells were centrifuged off.

Isolation of the product

The supernatant was concentrated by evaporation with a rotary evaporator to 200 ml and cooled to 0° C. The formed crystals were filtered off and dried. Altogether 0.34 mol (55.52 g) of 6-hydroxypyrazinecarboxylic acid sodium salt was able to be isolated, corresponding to a yield of 85 percent, relative to the pyrazinecarboxylic acid sodium salt used.

EXAMPLE 2

The cultivation of the biomass and the biotransformation took place corresponding to Example 1.

Isolation of the product but, after the centrifuging off of the cells, the supernatant was mixed with barium chloride dihydrate (0.25 ml; 61 g). The precipitate was filtered and dried. Altogether 0.18 mol (74.7 g) of di-6-hydroxypyrazinecarboxylic acid barium salt was isolated, corresponding to a yield of 90 percent, relative to the pyrazinecarboxylic acid sodium salt used.

TABLE 1

| Composition of the mineral salt medium | |
|---|---|
| $MgCl_2.6H_2O$ | 0.8 g/l |
| $CaCl_2$ | 0.16 g/l |
| $Na_2SO_4$ | 0.25 g/l |
| $KH_2PO_4$ | 0.4 g/l |
| $Na_2HPO_4$ | 0.9 g/l |
| SLF | 1 ml/l |
| FeEDTA | 15 ml/l |
| Composition of the trace elements (SLF) in the mineral salt medium | |
| KOH | 15 g/l |
| $EDTANa_2.2H_2O$ | 100 g/l |
| $ZnSO_4.7H_2O$ | 9 g/l |
| $MnCl_2.4H_2O$ | 4 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2$ | 0.18 g/l |

TABLE 1-continued

| | |
|---|---|
| $Na_2MoO_4.2H_2O$ | 0.2 g/l |
| Composition of FeEDTA | |
| $EDTANa_2.2H_2O$ | 5 g/l |
| $FeSO_4.7H_2O$ | 2 g/l |
| (The pH of the solution was adjusted to 7.0.) | |

What is claimed is:

1. A process for the production of 6-hydroxypyrazinecarboxylic acid or salt thereof comprising converting pyrazinecarboxylic acid or salt thereof into 6-hydroxypyrazinecarboxylic acid or salt thereof with *Alcaligenes faecalis* DSM No. 6269 or mutant thereof which is capable of the conversion and wherein said microorganism uses picolinic acid or salt thereof as the sole carbon, nitrogen, and energy source, and isolating the 6-hydroxypyrazinecarboxylic acid or salt thereof from the medium.

2. The process according to claim 1 wherein the reaction takes place with a single or continuous substrate addition, so that the substrate concentration does not exceed 20 percent by weight.

3. The process according to claim 2 wherein the reaction is performed under aerobic conditions at a pH of 4 to 10 and at a temperature of 10° to 60° C.

4. The process according to claim 3 wherein the 6-hydroxypyrazinecarboxylic acid is isolated in the form of a heavy soluble salt.

5. The process according to at claim 1 wherein the reaction takes place with a single or continuous substrate addition, so that the substrate concentration does not exceed 20 percent by weight.

6. The process according to claim 1 wherein the reaction is performed under aerobic conditions at a pH of 4 to 10 and at a temperature of 10° to 60° C.

7. The process according to claim 1 wherein the 6-hydroxypyrazinecarboxylic acid is isolated in the form of a slightly soluble salt.

* * * * *

UNITED STATES PATENT AND TRADEMARK OFFICE
CERTIFICATE OF CORRECTION

PATENT NO. : 5,238,829
DATED : Aug. 24, 1993
INVENTOR(S) : Kiener

It is certified that error appears in the above-identified patent and that said Letters Patent is hereby corrected as shown below:

On title page, item [19] "Keiner" should read --Kiener

In the title page, under [75] Inventor: delete "Keiner" and insert

--Kiener--.

Signed and Sealed this

Twelfth Day of April, 1994

Attest:

BRUCE LEHMAN

*Attesting Officer*     *Commissioner of Patents and Trademarks*